United States Patent
Berns et al.

(10) Patent No.: US 10,272,096 B2
(45) Date of Patent: Apr. 30, 2019

(54) METHODS AND SYSTEMS OF TREATING WOUNDS

(71) Applicant: The Regents of the University of California, Oakland, CA (US)

(72) Inventors: Michael W. Berns, Irvine, CA (US); Ryan M. Spitler, Costa Mesa, CA (US); Gerard Boss, La Jolla, CA (US)

(*) Notice: Subject to any disclaimer, the term of this patent is extended or adjusted under 35 U.S.C. 154(b) by 225 days.

(21) Appl. No.: 14/894,984

(22) PCT Filed: Jun. 6, 2014

(86) PCT No.: PCT/US2014/041385
§ 371 (c)(1),
(2) Date: Nov. 30, 2015

(87) PCT Pub. No.: WO2014/197847
PCT Pub. Date: Dec. 11, 2014

(65) Prior Publication Data
US 2016/0113941 A1     Apr. 28, 2016

Related U.S. Application Data

(60) Provisional application No. 61/832,700, filed on Jun. 7, 2013.

(51) Int. Cl.
| | | |
|---|---|---|
| A61K 31/555 | (2006.01) | |
| A61N 5/06 | (2006.01) | |
| A61K 9/00 | (2006.01) | |
| A61K 9/12 | (2006.01) | |
| A61N 5/067 | (2006.01) | |

(52) U.S. Cl.
CPC .......... *A61K 31/555* (2013.01); *A61K 9/0014* (2013.01); *A61K 9/12* (2013.01); *A61N 5/0613* (2013.01); *A61N 5/0616* (2013.01); *A61N 2005/067* (2013.01); *A61N 2005/0651* (2013.01); *A61N 2005/0659* (2013.01); *A61N 2005/0662* (2013.01)

(58) Field of Classification Search
CPC .................................................. A61K 31/555
See application file for complete search history.

(56) References Cited

U.S. PATENT DOCUMENTS

| | | | |
|---|---|---|---|
| 6,494,900 B1* | 12/2002 | Salansky | A61N 5/0616 606/13 |
| 2004/0162596 A1* | 8/2004 | Altshuler | A61N 5/0616 607/88 |
| 2008/0139991 A1 | 6/2008 | Street et al. | |
| 2010/0152153 A1 | 6/2010 | Boss et al. | |
| 2011/0028459 A1 | 2/2011 | Brown et al. | |

FOREIGN PATENT DOCUMENTS

EP    2 322 188    *   5/2011

OTHER PUBLICATIONS

Hamblin, M.R. The Role of Nitric Oxide in Low Level Light Therapy. In Mechanisms for Low-Light Therapy III, edited by Michael R. Hamblin, Ronald W. Waynant, and Juanita Anders, Proc. of SPIE vol. 6846, 684602, (2008).*
Silva et al. Evaluation of the Use of Low Level Laser and Photosensitizer Drugs in Healing. Lasers in Surgery and Medicine 34:451-457 (2004).*
Morita et al. Clinical Application of Low Reactive Level Laser Therapy (LLLT) for Atopic Dermatitis. Keio J. Med. 42(4): 174-176 (1993).*
The Merck Manual of Diagnosis and Therapy 17th ed. Beers et al., eds. Section 10, Dermatitis, pp. 777-793 (1999).*
Junior et al. J. Vas. Bras., 2007, vol. 6, No. 3, pp. 258-266 (Year: 2007).*
De Santana D.C.A.S. et al.; Nitric Oxide photorelease from hydrogels and from skin containing a nitro-ruthenuim complex; International Journal of Pharamceutics, vol. 391, No. 1, 21-28 (2010).
Amadeu. T. P. et al.; Nitric Oxide donor improves healing if applied on inflammatory and proliferative phase; Journal of Surgical Research, vol. 149, No. 1, 84-93, (2008).

* cited by examiner

*Primary Examiner* — James D. Anderson
(74) *Attorney, Agent, or Firm* — Accelerator AIX; Sean D. Senn

(57) ABSTRACT

The invention generally relates to methods for treating and/or reducing the severity of a wound in a subject. Provided are wound therapies combining low level light therapy (LLLT) and a nitric oxide (NO) donor to treat and/or reduce the severity of the wound. The LLLT and NO donor may be administered concurrently or sequentially. Also provided are wound treatment systems and kits including a light source and a NO donor, which are administered to a wounded subject. Further provided are pharmaceutical compositions that comprise a NO donor and are formulated to be administered in conjunction with LLLT.

20 Claims, 6 Drawing Sheets

METHODS AND SYSTEMS OF TREATING WOUNDS

CROSS REFERENCE TO RELATED APPLICATIONS

This application is a National Phase of International Application No. PCT/US2014/041385, filed Jun. 6, 2014, which designated the U.S. and that International Application was published under PCT Article 21(2) in English. This application also includes a claim of priority under 35 U.S.C. § 119(e) to U.S. Provisional Application No. 61/832,700, filed Jun. 7, 2013, the entirety of which is hereby incorporated by reference.

GOVERNMENT RIGHTS

The invention was made with government support under Grant Nos. FA9550-10-1-0538 and FA9550-08-1-0384 awarded by the AFOSR and Grant No. U01 NS058030 awarded by the National Institute of Neurological Diseases and Stroke. The Government has certain rights in this invention.

FIELD OF THE INVENTION

The invention generally relates to methods, systems, compositions, and kits for treating and/or reducing the severity of a wound.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The overall treatment of wounds may depend on the type, cause, and depth of the wound as well as whether or not other structures beyond the skin are involved. However, rapid and/or prolonged management of various wounds (e.g., chemical, thermal, or traumatic wounds), whether they are in the airway, on the skin, or elsewhere, is essential for successful mitigation of injury, and for personnel to return to useful service. For example, bacterial infection of a wound could impede the healing process and lead to life threatening complications. Low level light therapy (LLLT) is a promising modality for a variety of medical conditions, but the underlying mechanisms of LLLT may warrant further investigation and understanding. Thus, there is a need in the art for novel and effective treatments for wounds and bodily injuries.

SUMMARY OF THE INVENTION

Various embodiments of the present invention provide a method of treating and/or reducing the severity of a wound in a subject. The method may comprise providing a chemical compound; providing low level light therapy (LLLT); and administering a therapeutically effective amount of the chemical compound and LLLT to the subject, thereby treating and/or reducing the severity of the wound.

Various embodiments of the present invention provide a system for treating and/or reducing the severity of a wound in a subject. The system may include a light source that emits low level phototherapy light; and a chemical compound.

Various embodiments of the present invention provide a kit for treating and/or reducing the severity of a wound in a subject. The kit may include a light source that emits low level phototherapy light; a chemical compound; and instructions for using the light source and the chemical compound to treat a wound in a subject.

Various embodiments of the present invention provide a composition for treating and/or reducing the severity of a wound in a subject. The composition may comprise a nitric oxide donor. In some embodiments, the composition further comprises a suitable carrier. Examples of the suitable carrier include but are not limited to a time release hydrogel and an aerosol spray.

In various embodiments, the wound is chemical, thermal, mechanical or traumatic wound, or a combination thereof. In various embodiments, the chemical compound is a nitric oxide donor. Examples of the nitric oxide donor include but are not limited to nitrosyl-cobinamide (NO-Cbi), and its functional equivalents, analogs, derivatives, and salts. In certain embodiments, the nitric oxide is administered topically to the wound. Examples of topical administration forms include but are not limited to time release hydrogels, aerosol sprays, lotions, creams, ointments, and gels.

In various embodiments, the light source of the LLLT is a laser or a LED, or a combination thereof. In various embodiments, the light source of the LLLT has a bandwidth of about 1-5, 5-10, 10-20, 20-30, 30-40, 40-50, 50-60, 60-70, 70-80, 80-90, or 90-100 nm. In various embodiments, the light source has a wavelength of about 500-600, 600-700, 700-800, 800-900, or 900-1000 nm, or a combination thereof.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DETAILED DESCRIPTION OF THE INVENTION

Figure 1:
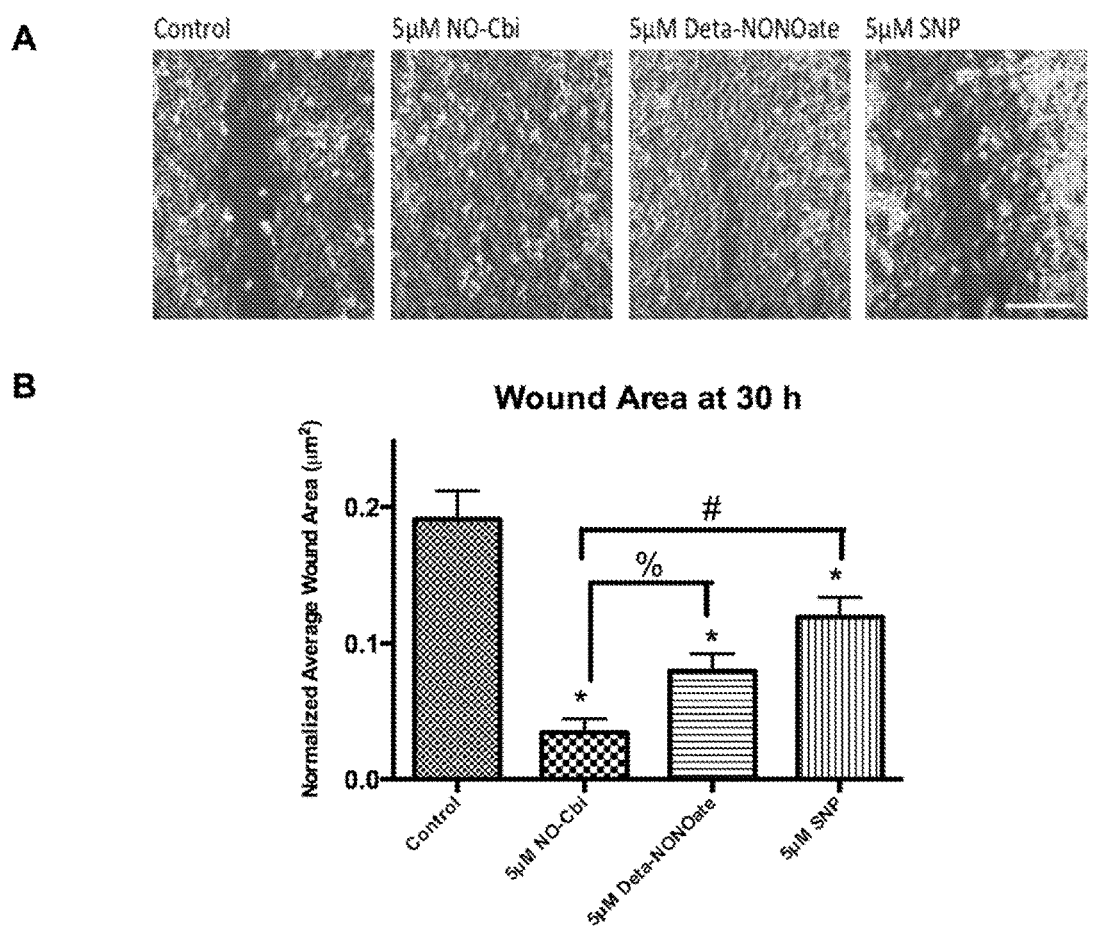
FIG. 1 depicts, in accordance with various embodiments of the invention, NO-Cbi increases wound healing and migration in A-549 cells. (A) Mechanical scratch wounds were generated in a monolayer of A-549 cells, and 30 hours later, the area of the wound was evaluated by custom computer-based software. At 0, 4, 9, and 24 hour post wounding, cells received fresh medium with 5 uM of NO-Cbl, Deta-NONOate, sodium nitroprusside (SNP), or fresh medium alone. (B) The normalized average wound area was determined by dividing the final wound area by the initial wound area and averaging replicates. Data represent the mean+/−SEM of at least 3 separate experiments with an n=12 in each experiment.

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22$^{nd}$ ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3$^{rd}$ ed., revised ed., J. Wiley & Sons (New York, N.Y. 2006); Smith, March's Advanced Organic Chemistry Reactions, Mechanisms and Structure 7$^{th}$ ed., J. Wiley & Sons (New York, N.Y. 2013); Singleton, Dictionary of DNA and Genome Technology 3$^{rd}$ ed., Wiley-Blackwell (Nov. 28, 2012); and Green and Sambrook, Molecular Cloning: A Laboratory Manual 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies A Laboratory Manual 2$^{nd}$ ed., Cold Spring Harbor Press (Cold Spring Harbor N.Y., 2013); Köhler and Milstein, Derivation of specific antibody-producing tissue culture and tumor lines by cell fusion, Eur. J. Immunol. 1976 July, 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of various wounds, delay or slowing of various wounds, and amelioration or palliation of symptoms associated with various wounds.

"Conditions" and "disease conditions," as used herein may include, but are in no way limited to any form of wounds or wound-related condition, disease or disorder. Examples of wounds include but are not limited to chemical, thermal, mechanical and traumatic wounds.

As used herein, the term "administering," refers to the placement an agent as disclosed herein into a subject by a method or route which results in at least partial localization of the agents at a desired site. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein.

The term "sample" or "biological sample" as used herein denotes a sample taken or isolated from a biological organism, e.g., a tumor sample from a subject. Exemplary biological samples include, but are not limited to, a biofluid sample; serum; plasma; urine; saliva; a tumor sample; a tumor biopsy and/or tissue sample etc. The term also includes a mixture of the above-mentioned samples. The term "sample" also includes untreated or pretreated (or pre-processed) biological samples. In some embodiments, a sample can comprise one or more cells from the subject.

As used herein, a "subject" means a human or animal. Usually the animal is a vertebrate such as a primate, rodent, domestic animal or game animal Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., various wounds) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "statistically significant" or "significantly" refers to statistical evidence that there is a difference. It is defined as the probability of making a decision to reject the null hypothesis when the null hypothesis is actually true. The decision is often made using the p-value.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

Unless otherwise defined herein, scientific and technical terms used in connection with the present application shall have the meanings that are commonly understood by those of ordinary skill in the art to which this disclosure belongs.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

As further described herein, low level light therapy (LLLT) has numerous therapeutic benefits, including improving wound healing, but the precise mechanisms involved are not well-established; in particular, the underlying role of cytochrome C oxidase (C-ox) as the primary photoacceptor and the associated biochemical mechanisms still require further investigation. The inventors demonstrated that the nitric oxide (NO) donating drug nitrosyl-cobinamide (NO-Cbi) enhances wound healing through a cGMP/cGMP-dependent protein kinase/Erk mechanism. Herein, the inventors further show that the combination of LLLT and NO-Cbi markedly improve wound healing compared to either treatment alone. LLLT-enhanced wound healing proceeded through an electron transport chain-C-ox-dependent mechanism with reduction of reactive oxygen species (ROS) and increased ATP production. C-ox was validated as the primary photo-acceptor by three observations: increased oxygen consumption, reduced wound healing in the presence of sodium azide, and disassociation of cyanide, a known C-ox ligand, following LLLT. The inventors conclude that LLLT and NO-Cbi accelerate wound healing through two independent mechanisms, the electron transport chain-C-ox pathway and cGMP/Erk signaling, respectively.

In accordance with various embodiments herein, an important aspect of the mechanism is validating the photo-acceptor molecule, because an absorbing molecule is necessary for light energy to be converted into chemical energy that can be used by cells. The multimolecular complexes of the electron transport system have been suggested as the light receptors, and that light increases metabolic activity. LLLT increases mitochondrial activity of complexes I, II, III, IV and succinate dehydrogenase, with cytochrome C oxidase (C-ox), part of complex IV, generally accepted as the primary photo-accepting molecule. Evidence for a C-ox-dependent LLLT mechanism includes increased oxygen consumption during LLLT—the majority of total cellular oxygen consumption occurs at complex IV, and the absorption spectrum of C-ox intermediates are similar to the known action spectra of LLLT. Changes in reactive oxygen species (ROS) have also been reported, as well as increases in ATP production. Increased cellular nitric oxide (NO) also occurs from either NO release from metal complexes or up-regulation of inducible NO synthase (iNOS).

The inventors further validated C-ox as the primary photo-acceptor because: (1) LLLT increases cellular oxygen consumption, (2) C-ox inhibition reverses wound healing induced by LLLT, and (3) LLLT decreases the intracellular concentration of cyanide, a known ligand of C-ox. Other observations include a reduction of cellular ROS and an increase in ATP production, which implies more efficient electron flow through the electron transport chain.

The inventors demonstrated increased wound healing by either light or nitrosyl-cobinamide (NO-Cbi). Herein, the inventors demonstrate that the combination of LLLT and NO-Cbi produces much greater wound healing than either treatment alone. In addition, the inventors show that the functional response of each modality proceeds through a different biochemical pathway: the electron transport chain and Erk signaling, respectively.

As disclosed herein, the inventors combined drug and light technology for the purpose of accelerating the healing of wounds on the skin, ulcers, and elsewhere in the body. By combining both methods, the inventors were able to achieve more rapid healing than either applied alone, demonstrating that the drug and light act synergistically. The drug (NO-Cbi) is a direct nitric oxide releasing drug which can be developed in both a gel release form and an aerosolized form so that it can be easily applied. This may be done either before, after, or during exposure to about 600-900 nm light. The light may be from a diode array that may be developed specifically for this purpose. For example, it could be used to accelerate healing in burns, traumatic injury such as severe abrasions, and surgical wound healing.

In one embodiment the present invention provides a method of treating a wound in a subject. The method comprises: providing a chemical compound; providing low level light therapy; and treating the wound by administering a therapeutically effective dosage of the chemical compound and low level light therapy to the subject. In another embodiment, the chemical compound is a nitric oxide donor. In another embodiment, the chemical compound is nitrosyl-cobinamide (NO-Cbi). In another embodiment, the chemical compound is released in a time release hydrogel. In another embodiment, the chemical compound is released as an aerosol. In another embodiment, the low level light therapy is administered at a wavelength of about 600-900 nm. In another embodiment, the chemical compound is administered at a dosage between 3 to 10 µM. In another embodiment, the subject is a mouse or rat. In another embodiment, the subject is a human.

In another embodiment, the present invention provides an apparatus comprising a laser and/or diode system that emits low level phototherapy light, and an aerosol spray of a chemical compound. In another embodiment, the chemical compound is nitrosyl-cobinamide (NO-Cbi).

In another embodiment, the present invention provides a composition comprising a nitric oxide donor, and a suitable carrier. In another embodiment, the suitable carrier is an aerosol spray. In another embodiment, the suitable carrier is a time release hydrogel. In another embodiment, the composition is adapted to be administered in conjunction with low level light therapy. In another embodiment, the nitric oxide donor is nitrosyl-cobinamide (NO-Cbi).

Treatment Methods

In various embodiments, the present invention provides a method of treating a wound in a subject. The method may consist of or may consist essentially of or may comprise: providing a chemical compound; providing low level light therapy (LLLT); and administering a therapeutically effective amount of the chemical compound and LLLT to the subject, thereby treating the wound.

In various embodiments, the wound is chemical, thermal, mechanical or traumatic wound, or a combination thereof. In various embodiments, the subject is a human. In various embodiments, the subject is a mammalian subject including but not limited to human, monkey, ape, dog, cat, cow, horse, goat, pig, rabbit, mouse and rat.

In various embodiments, the chemical compound is a nitric oxide donor. Examples of the nitric oxide donor include but are not limited to nitrosyl-cobinamide (NO-Cbi), NO gas, organic nitrate, glyceryl trinitrate (GTN, nitroglycerin), amyl nitrite, isosorbide dinitrate, isosorbide mononitrate (ISMN), pentaerythrityl tetranitrate (PETN), sodium nitroprusside (SNP), sodium trioxodinitrate (Angeli's salt), p-nitrosophosphate compound (—NO heterodienophile), BiDil (isosorbide dinitrate with hydralazine), diazeniumdiolate (NONOate), diethylamine NONOate (DEA/NO), Spermine NONOate (SPER/NO), MAHMA/NO, PROLI/NO, V-PYRRO/NO, S-nitrosothiol, S-nitroso-glutathione (GSNO), S-nitroso-N-acetylpenicillamine (SNAP), S-nitroso-N-valerylpenicillamine (SNVP), S-nitrosoalbumin, S-nitroso-cysteine, S—NO—N-acetyl-L-cysteine, Hybrid NO donor drug, NO-NSAID, NicOx compound, nitroaspirin, NCX4016, NCX4215, nicorandil, Nipradilol (K-351), nitro-pravastatin, NCX6550, nitro-fluvastatin, SNO-diclofenac, SNO-captopril, furoxan bound to 4-phenyl-1,4-dihydropyridine, ion-exchanged zeolite, NO-zeolite, 3-morpholinosydnonimine, molsidomine, the functional equivalents, analogs, derivatives, and salts of these reagents, and their various combinations. Additional information can be found in Miller et al. (Recent developments in nitric oxide donor drugs; Br J Pharmacol. June 2007; 151(3): 305-321), Al-Sa'doni et al. (S-Nitrosothiols: a class of nitric oxide-donor drugs; Clin Sci (Lond). 2000 May; 98(5):507-20), Ignarro et al. (Nitric oxide donors and cardiovascular agents modulating the bioactivity of nitric oxide: an overview; Circ Res. 2002 Jan. 11; 90(1):21-8), and Boss et al. (Nitric oxide releasing compounds, U.S. Pat. No. 8,222,242, Jul. 17, 2012), which are incorporated herein by reference in their entirety as though fully set forth. In certain embodiments, the nitric oxide donor is nitrosyl-cobinamide (NO-Cbi), or a functional equivalent, analog, derivative, or salt thereof.

Typical dosages of an effective amount of the chemical compound (for example, the nitric oxide donor) can be in the ranges recommended by the manufacturer where known therapeutic compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the chemical compound may be administered once a day (SID/QD), twice a day (BID), three times a day (TID), four times a day (QID), or more, so as to administer an effective amount of the chemical compound to the subject, where the effective amount is any one or more of the doses described herein.

In various embodiments, the chemical compound is administered at about 0.1-1, 1-5, 5-10, 10-20, or 20-30 µM. In some embodiments, the chemical compound is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. Here, "mg/kg" refers to mg chemical compound per kg body weight of the subject. In other embodiments, the chemical compound is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/cm$^2$, or a combination thereof. Here, "mg/cm$^2$" refers to mg chemical compound per cm$^2$ wound area in the subject. In various embodiments, the chemical compound is administered once, twice, three or more times. In various embodiments, the chemical compound is administered about 1-3 times per day, 1-7 times per week, or 1-9 times per month. In various embodiments, the chemical compound is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In various embodiments, the chemical compound is a nitric oxide donor. In certain embodiments, the nitric oxide donor is nitrosyl-cobinamide (NO-Cbi), or a functional equivalent, analog, derivative, or salt thereof.

In accordance with the invention, the chemical compound (for example, the nitric oxide donor) may be administered using the appropriate modes of administration, for instance, the modes of administration recommended by the manufacturer. In accordance with the invention, various routes may be utilized to administer the chemical compound of the claimed methods, including but not limited to aerosol, nasal, oral, transmucosal, transdermal, parenteral, implantable pump, continuous infusion, topical application, capsules and/or injections. In various embodiments, the chemical compound is administered topically, intravascularly, intravenously, intraarterially, intramuscularly, subcutaneously, intraperitoneally, intranasally, or orally.

In various embodiments, the chemical compound is provided in a pharmaceutical composition. In one embodiment, the chemical compound is provided in a time release hydrogel. In another embodiment, the chemical compound is provided in an aerosol spray.

In various embodiments, the light source of the LLLT is a laser or a LED, or a combination thereof. In one embodiment, the light source of the LLLT has a bandwidth of about 1-5, 5-10, 10-20, 20-30, 30-40, 40-50, 50-60, 60-70, 70-80, 80-90, or 90-100 nm.

In various embodiments, the LLLT is administered at a wavelength of about 600-900 nm. In some embodiments, the LLLT is administered at a wavelength of about 500-600, 600-700, 700-800, 800-900, or 900-1000 nm, or a combination thereof. In some embodiments, the LLLT is administered at a wavelength of about 600-620, 620-640, 640-660, 660-680, or 680-700 nm, or a combination thereof. In some embodiments, the LLLT is administered at a wavelength of about 700-720, 720-740, 740-760, 760-780, or 780-800 nm, or a combination thereof. In some embodiments, the LLLT is administered at a wavelength of about 800-820, 820-840, 840-860, 860-880, or 880-900 nm, or a combination thereof. In some embodiments, the LLLT is administered at a wavelength of about 900-920, 920-940, 940-960, 960-980, or 980-1000 nm, or a combination thereof.

In various embodiments, the LLLT is administered at a power density of about 0.1-1, 1-5, 5-10, 10-20, or 20-30 mW/cm2. In various embodiments, the LLLT is administered for about 1-10, 10-20, 20-30, 30-40, 40-50, or 50-60 minutes. In various embodiments, the LLLT is administered for about 1-6, 6-12, 12-18, or 18-24 hours. In certain embodiments, the LLLT is administered at an energy density of about 1-5, 5-10, 10-20, 20-30, 30-40, 40-50, 50-60, 60-70, 70-80, 80-90, or 90-100 J/cm$^2$.

In various embodiments, the wound is kept under low level light or in the dark before and/or after LLLT. In some embodiments, the LLLT and the chemical compound are administered concurrently. In other embodiments, the LLLT and the chemical compound are administered sequentially. In accordance with the present invention, the LLLT may be administered before, during or after administering the chemical compound. In certain embodiments, the LLLT is administered about 0.1-0.5, 0.5-1, 1-6, 6-12, 12-18, or 18-24 hours before administering the chemical compound. In some embodiments, the chemical compound is administered about 0.1-0.5, 0.5-1, 1-6, 6-12, 12-18, or 18-24 hours after administering the LLLT.

Treatment Systems and Kits

In various embodiments, the present invention provides a system. The system may consist of or may consist essentially of or may comprise: a light source that emits low level phototherapy light; and a chemical compound.

In certain embodiments, the system described herein is used to treat a wound in a subject. In accordance with the present invention, the wound is chemical, thermal, mechanical or traumatic wound, or a combination thereof. In accordance with the present invention, the subject is a human. Still in accordance with the present invention, the subject is a mammalian subject including but not limited to human, monkey, ape, dog, cat, cow, horse, goat, pig, rabbit, mouse and rat. To treat the wound in the subject, the low level light emitted from the light source is directed to the wound (i.e., low level light therapy; LLLT) and the chemical compound is administered to the subject. The LLLT may be conducted before, during, or after administering the chemical compound to the subject. In some embodiments, the LLLT may be conducted about 0.1-0.5, 0.5-1, 1-6, 6-12, 12-18, or 18-24 hours before administering the chemical compound to the subject. In some embodiments, the chemical compound is administered about 0.1-0.5, 0.5-1, 1-6, 6-12, 12-18, or 18-24 hours after conducting the LLLT. In various embodiments, the LLLT is conducted for about 1-10, 10-20, 20-30, 30-40, 40-50, or 50-60 minutes. In various embodiments, the LLLT is conducted for about 1-6, 6-12, 12-18, or 18-24 hours.

In various embodiments, the chemical compound is administered at about 0.1-1, 1-5, 5-10, 10-20, or 20-30 μM. In some embodiments, the chemical compound is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. Here, "mg/kg" refers to mg chemical compound per kg body weight of the subject. In other embodiments, the chemical compound is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/cm$^2$, or a combination thereof. Here, "mg/cm$^2$" refers to mg chemical compound per cm$^2$ wound area in the subject. In various embodiments, the chemical compound is administered once, twice, three or more times. In various embodiments, the chemical compound is administered about 1-3 times per day, 1-7 times per week, or 1-9 times per month. In various embodiments, the chemical compound is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In various embodiments, the chemical compound is a nitric oxide donor. In certain embodiments, the nitric oxide donor is nitrosyl-cobinamide (NO-Cbi), or a functional equivalent, analog, derivative, or salt thereof.

In accordance with the invention, the chemical compound may be administered using the appropriate modes of administration, for instance, the modes of administration recommended by the manufacturer. In accordance with the invention, various routes may be utilized to administer the chemical compound of the claimed methods, including but not limited to aerosol, nasal, oral, transmucosal, transdermal, parenteral, implantable pump, continuous infusion, topical application, capsules and/or injections. In various embodiments, the chemical compound is administered topically, intravascularly, intravenously, intraarterially, intramuscularly, subcutaneously, intraperitoneally, intranasally, or orally.

In various embodiments, the chemical compound is provided in a pharmaceutical composition. In one embodiment, the chemical compound is provided in a time release hydrogel. In another embodiment, the chemical compound is provided in an aerosol spray.

In various embodiments, the chemical compound is a nitric oxide donor. Examples of the nitric oxide donor include but are not limited to nitrosyl-cobinamide (NO-Cbi), NO gas, organic nitrate, glyceryl trinitrate (GTN, nitroglycerin), amyl nitrite, isosorbide dinitrate, isosorbide mononitrate (ISMN), pentaerythrityl tetranitrate (PETN), sodium nitroprusside (SNP), sodium trioxodinitrate (Angeli's salt), p-nitrosophosphate compound (—NO heterodienophile), BiDil (isosorbide dinitrate with hydralazine), diazeniumdiolate (NONOate), diethylamine NONOate (DEA/NO), Spermine NONOate (SPER/NO), MAHMA/NO, PROLI/NO, V-PYRRO/NO, S-nitrosothiol, S-nitroso-glutathione (GSNO), S-nitroso-N-acetylpenicillamine (SNAP), S-nitroso-N-valerylpenicillamine (SNVP), S-nitrosoalbumin, S-nitroso-cysteine, S—NO—N-acetyl-L-cysteine, Hybrid NO donor drug, NO-NSAID, NicOx compound, nitroaspirin, NCX4016, NCX4215, nicorandil, Nipradilol (K-351), nitro-pravastatin, NCX6550, nitro-fluvastatin, SNO-diclofenac, SNO-captopril, furoxan bound to 4-phenyl-1,4-dihydropyridine, ion-exchanged zeolite, NO-zeolite, 3-morpholinosydnonimine, molsidomine, the functional equivalents, analogs, derivatives, and salts of these reagents, and their various combinations. Additional information can be found in Miller et al. (Recent developments in nitric oxide donor drugs; Br J Pharmacol. June 2007; 151(3): 305-321), Al-Sa'doni et al. (S-Nitrosothiols: a class of nitric oxide-donor drugs; Clin Sci (Lond). 2000 May; 98(5):507-20), Ignarro et al. (Nitric oxide donors and cardiovascular agents modulating the bioactivity of nitric oxide: an overview; Circ Res. 2002 Jan. 11; 90(1):21-8), and Boss et al. (Nitric oxide releasing compounds, U.S. Pat. No. 8,222,242, Jul. 17, 2012), which are incorporated herein by reference in their entirety as though fully set forth. In certain embodiments, the nitric oxide donor is nitrosyl-cobinamide (NO-Cbi), or a functional equivalent, analog, derivative, or salt thereof.

In various embodiments, the light source is a laser, LED, or diode system, or a combination thereof. In various embodiments, the light source has a bandwidth of about 1-5, 5-10, 10-20, 20-30, 30-40, 40-50, 50-60, 60-70, 70-80, 80-90, or 90-100 nm. In various embodiments, the light source has a wavelength of about 500-600, 600-700, 700-800, 800-900, or 900-1000 nm, or a combination thereof. In some embodiments, the light source has a wavelength of about 600-620, 620-640, 640-660, 660-680, or 680-700 nm, or a combination thereof. In some embodiments, the light source has a wavelength of about 700-720, 720-740, 740-760, 760-780, or 780-800 nm, or a combination thereof. In some embodiments, the light source has a wavelength of about 800-820, 820-840, 840-860, 860-880, or 880-900 nm, or a combination thereof. In some embodiments, the light source has a wavelength of about 900-920, 920-940, 940-960, 960-980, or 980-1000 nm, or a combination thereof. In various embodiments, the light source has a power density of about 0.1-1, 1-5, 5-10, 10-20, or 20-30 mW/cm2. In various embodiments, the light source has an energy density of about 1-5, 5-10, 10-20, 20-30, 30-40, 40-50, 50-60, 60-70, 70-80, 80-90, or 90-100 J/cm$^2$.

In various embodiments, the present invention provides a kit for treating a wound in a subject. The kit is an assemblage of materials or components, including at least one of the inventive components. The kit may consist of or may consist essentially of or may comprise: a light source that emits low level phototherapy light; a chemical compound; and instructions for using the light source and the chemical compound to treat a wound in a subject.

The exact nature of the components configured in the inventive kit depends on its intended purpose. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to affect a desired outcome. Optionally, the kit also contains other useful components, such as, spray bottles or cans, diluents, buffers, pharmaceutically acceptable carriers, syringes, catheters, applicators (for example, applicators of cream, gel or lotion etc.), pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the chemical compound can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of a composition as described herein. The packaging material generally has an external label which indicates the contents and/or purpose of the kit and/or its components.

Pharmaceutical Compositions

In various embodiments, the present invention provides a composition that may consist of or may consist essentially of or may comprise a nitric oxide donor. In accordance with the present invention, the composition may be used for treating a wound. In some embodiments, the composition further comprises a suitable carrier. Examples of the suitable carrier include but are not limited to a time release hydrogel and an aerosol spray.

Examples of the nitric oxide donor include but are not limited to nitrosyl-cobinamide (NO-Cbi), NO gas, organic nitrate, glyceryl trinitrate (GTN, nitroglycerin), amyl nitrite, isosorbide dinitrate, isosorbide mononitrate (ISMN), pentaerythrityl tetranitrate (PETN), sodium nitroprusside (SNP), sodium trioxodinitrate (Angeli's salt), p-nitrosophosphate compound (—NO heterodienophile), BiDil (isosorbide dinitrate with hydralazine), diazeniumdiolate (NONOate), diethylamine NONOate (DEA/NO), Spermine NONOate (SPER/NO), MAHMA/NO, PROLI/NO, V-PYRRO/NO, S-nitrosothiol, S-nitroso-glutathione (GSNO), S-nitroso-N-acetylpenicillamine (SNAP), S-nitroso-N-valerylpenicillamine (SNVP), S-nitrosoalbumin, S-nitroso-cysteine, S—NO—N-acetyl-L-cysteine, Hybrid NO donor drug, NO-NSAID, NicOx compound, nitroaspirin, NCX4016, NCX4215, nicorandil, Nipradilol (K-351), nitro-pravastatin, NCX6550, nitro-fluvastatin, SNO-diclofenac, SNO-captopril, furoxan bound to 4-phenyl-1,4-dihydropyridine, ion-exchanged zeolite, NO-zeolite, 3-morpholinosydnonimine, molsidomine, the functional equivalents, analogs, derivatives, and salts of these reagents, and their various combinations. Additional information can be found in Miller et al. (Recent developments in nitric oxide donor drugs; Br J Pharmacol. June 2007; 151(3): 305-321), Al-Sa'doni et al. (S-Nitrosothiols: a class of nitric oxide-donor drugs; Clin Sci (Lond). 2000 May; 98(5):507-20), Ignarro et al. (Nitric oxide donors and cardiovascular agents modulating the bioactivity of nitric oxide: an overview; Circ Res. 2002 Jan. 11; 90(1):21-8), and Boss et al. (Nitric oxide releasing compounds, U.S. Pat. No. 8,222,242, Jul. 17, 2012), which are incorporated herein by reference in their entirety as though fully set forth. In certain embodiments, the nitric oxide donor is nitrosyl-cobinamide (NO-Cbi), or a functional equivalent, analog, derivative, or salt thereof.

In various embodiments, the nitric oxide donor in the composition is provided at about 0.1-1, 1-5, 5-10, 10-20, or 20-30 µM. In various embodiments, the nitric oxide donor in the composition is provided in mg per kilogram body weight of the subject; for example, about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg. In various embodiments, the nitric oxide donor in the composition is provided in mg per cm2 wound area in the subject; for example, about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/cm2.

In various embodiments, the composition is formulated to be administered in conjunction with LLLT. In various embodiments, the composition is formulated for topical, intravascular, intravenous, intraarterial, intratumoral, intramuscular, subcutaneous, intraperitoneal, oral, intranasal or via inhalation administration. In certain embodiments, the composition is administered as a time release hydrogel or an aerosol spray.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. Methods for these administrations are known to one skilled in the art.

In various embodiments, the composition is administered 1-3 times per day, 1-7 times per week, or 1-9 times per month. In various embodiments, the composition is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In various embodiments, the composition is administered once, twice, three or more times. In various embodiments, the composition may be administered once a day (SID/QD), twice a day (BID), three times a day (TID), four times a day (QID), or more, so as to administer an effective amount of the nitric oxide donor to the subject, where the effective amount is any one or more of the doses described herein.

In various embodiments, the compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving dry milling, mixing, and blending for powder forms; milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins P A, USA) (2000).

Before administration to patients, formulants may be added to the composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

Polymers formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

The pharmaceutical composition according to the invention can also be a bead system for delivering the therapeutic agent to the target cells. For example, pectin/zein hydrogel bead system may be used to deliver Neuregulin-4 or a pharmaceutical equivalent, analog, derivative or a salt thereof, to the target cells in the subject (Yan F. et al., J Clin Invest. 2011 June; 121(6):2242-53).

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Overview

The inventors determined that Nitrosyl-Cobinamide (NO-Cbi) accelerates wound healing at optimal doses, and combined the NO-Cbi induced wound healing with low level phototherapy to achieve even faster wound healing in cells and animals. Concomitant with cell and animal studies, an aerosol formulation for application of NO-Cbi to airways may be formulated, and a time-release gel may be developed that can be used for the treatment of burn wounds and for example other traumatic injury on the battlefield, in field hospitals, or in rehabilitation centers. Photonic systems may be used for analysis/monitoring wound repair, elucidating pharmacological mechanisms of action of the No-Cbi, and as combined therapy with NO-Cbi.

Figure 2:
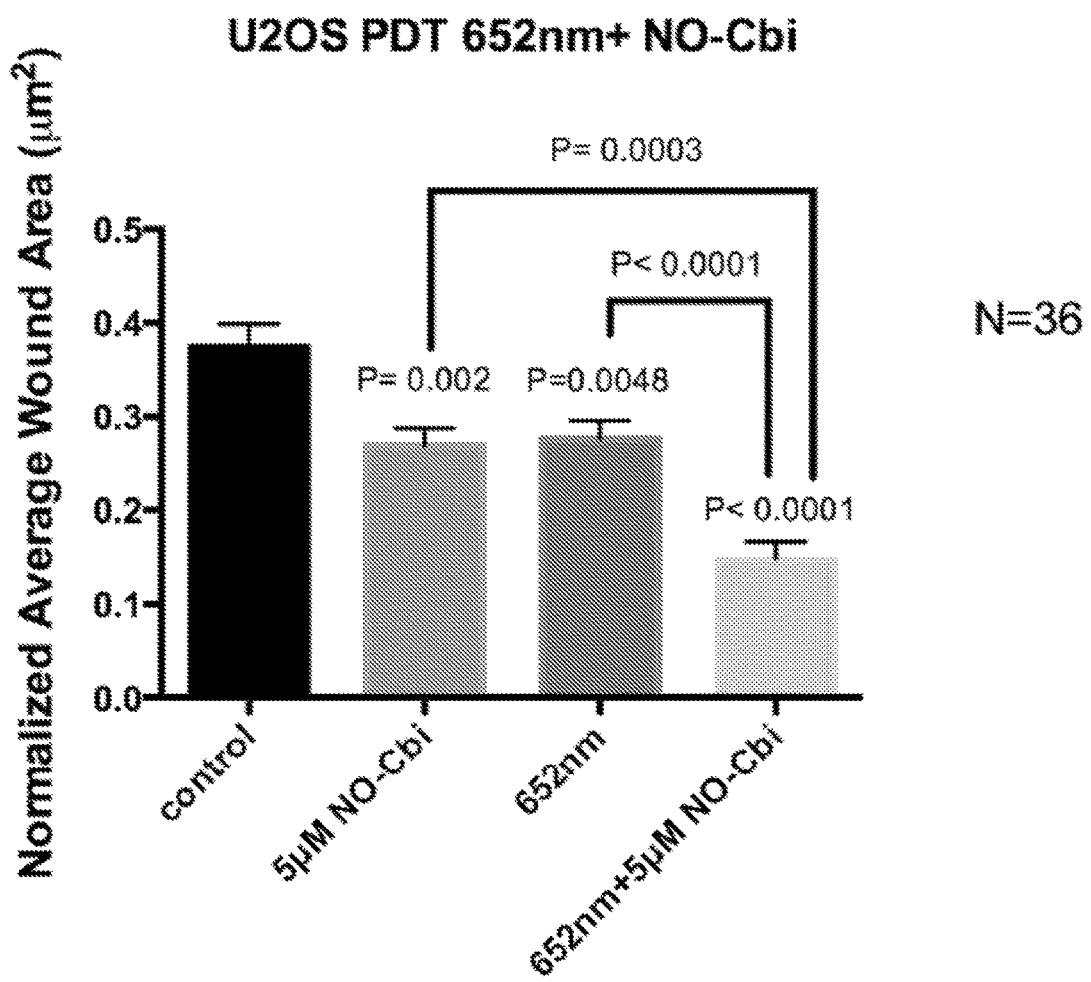
FIG. 2 depicts, in accordance with various embodiments of the invention, that combination of drug and light technology results in accelerated healing of wounds. This is evidenced by combination of NO-Cbi and light technology resulting in more rapid healing than either applied alone.

The inventors have shown that NO-Cbi improved in vitro wound healing in several different cell systems, including lung epithelial cells, primary human lung fibroblasts, and in a cancer cell model. On a molar basis, NO-Cbi was more effective than two other NO donors (FIG. 1 herein), with the effective NO-Cbi dose ranging from 3 to 10 uM, depending on the cell type. The inventors established this optimal dose range in order to provide a reasonable dose for actual treatment of airway injury. Mechanistically, the inventors determined that improved wound healing was from increased cell migration and not cell proliferation (division). The inventors found that the effect of NO-Cbi was mainly through cGMP-dependent protein kinase (PKG) type I, as determined using pharmacological inhibitors and activators, and siRNAs targeting PKG type I and II. The inventors concluded that NO-Cbi is a potent inducer of cell migration and wound closure, acting via cGMP, and requiring PKG type I and II. Further, as depicted in FIG. 2 herein, the inventors combined NO-Cbi and light technology, resulting in more rapid healing than either applied alone.

Example 2

Acceleration of Wound Healing by a Nitric Oxide Donor and Low Level Phototherapy Further cellular mechanistic pharmacological studies may be completed before animal and human studies are started. These may involve characterization of NO uptake by epithelial cells and subsequent activation of Rho GTPases, and coupling GTPase activation with cellular metabolism during the wound healing process. A NO sensitive dye, DAF-FM, may be used to assess the uptake of NO during wound closure. This study may determine if cells at the leading edge of the wound absorb NO differently than cells further from the wound site, and if there is any sub-cellular localization, as NO and NO-Cbi can diffuse through the cell membrane. After NO stimulation, activation of these proteins may be monitored live using FRET (fluorescence resonance energy transfer) biosensors. These novel photonic biosensors have distinct emission spectra that correspond to the active GTP bound state or inactive GDP bound state. Thus, real-time in-vitro monitoring will provide specific spatial and temporal information regarding the state of cell motility molecules Rac 1, cdc42 RhoA, which are integral to the healing process. The inventors may correlate enhanced cell migration from NO stimulation with the activation states of the Rho GTPases. Of particular interest is Raci, which is also a component of the NADPH oxidase complex which can be measured in real-time using FLIM (fluorescent lifetime imaging microscopy). FLIM and FRET measurements allow monitoring of the metabolic state of the cells throughout the course of wound healing, thus, potentially optimizing wound healing in vivo on an individual patient basis. The mechanistic studies also provide pharmacology for animal & human studies, and for the FDA.

The use of low level phototherapy light (LLP) was first studied by Karu and colleagues in 1989, and was based on activation of the metabolism of the mitochondrial aerobic respiration pathway. LLT does work in certain situations, especially in activating cell migration and proliferation, and stimulation of cytokines and growth factors necessary for wound healing. Since the 600-900 nm wavelengths used are readily available in different laser and diode systems (and are sold commercially for LLT), and the dosimetry for a variety of wound healing scenarios has been determined, several different LLT wavelengths may be applied to the cell wound healing models alone, and in combination with the NO-Cbi. There is synergy between these two methods, with the mechanisms of action different. The combined NO-Cbi treatment and LLT will be applied to in vivo systems.

NO-Cbi alone, NO-Cbi with LLT, and LLT alone may be further tested in two animal wound healing systems. In addition, the application of the NO-Cbi may be used and tested in a time release hydrogel, and in an aerosol spray. One wound model may be rat thermal burns. Two types of burns may be made: (1) superficial-partial thickness burns that extend to the upper layers of the papillary dermis, and naturally heal in 2 to 3 weeks, and (2) full thickness burns that extend through the papillary epidermis, and heal over a period. Both the hydrogel and aerosol application of NO-Cbi may be used to develop an aerosol application for airway injury, and it may prove effective (and easier to apply in a combat situation, for example) for the skin wounds as well. Another wound model may be a simple scratch assay on the skin of the rats since the epithelial layer of the rat is only 2-3 cells layers thick.

As in the burn study, both the gel and aerosol sprays may be used, the latter providing data that can be applied in future airway studies. Analysis/diagnostics of both thermal burn and scratch wounds may involve two photonic methods: (1) real time imaging using WiFI methods, (2) live microscopic multiphoton imaging. In addition, histopathological tissue analysis may be done using core BLI resources. Utilization of the burn and scratch assay studies, determination of the pharmacological mechanism of action and the potential use of LLT to further enhance wound healing, may further result in a comprehensive picture of the efficacy of the time-release NO-Cbi gel, and the NO-Cbi aerosol to promote enhanced wound healing Animal studies may involve multiple replicates in order to provide statistically significant results. Experimental and controls may be: (1) scratch and burn wounds that are untreated, (2) treated with the hydrogel and/or aerosol minus the NO-Cbi, (3) treated with the hydrogel and/or aerosol plus the NO-Cbi, (4) LLT alone, (5) LLT plus the NO-Cbi.

Example 3

The inventors demonstrate that combination therapy of NO-Cbi and LLLT accelerates wound healing greater than either treatment alone; that C-ox has been further validated as the primary photo-accepting molecule; and that the combination therapy of NO-Cbi and LLLT accelerates wound healing through the electron transport chain-C-ox pathway and cGMP/Erk signaling, respectively.

Cell Culture

U2OS human osteosarcoma cells were obtained from the American Type Tissue Culture Collection (ATCC, Rockville, Md.). Cells were grown in T-75 flasks (Corning, Fisher, Pittsburgh, Pa.) in a 37° C., 5% $CO_2$/95% air incubator using Dulbecco's Modified Eagle's Medium (DMEM) and supplemented with 10% fetal bovine serum (Mediatach, Manassas, Va.). Cells were trypsinized with TrypLE (Invitrogen Life Technologies, Carsbad, Calif.), seeded into 6-well or 96-well plates (Corning, Fisher, Pittsburgh, Pa.) and grown to confluence.

Light Irradiation Devices

The light sources and parameters of delivery were previously described (see Spitler et al., Comparison of laser and diode sources for acceleration of in vitro wound healing by low-level light therapy, Journal of biomedical optics 2014, 19(3):38001). Briefly two light sources were used, a laser (Biolitec AG, Jena, Germany) and a LED array (Biophotas Inc., Tustin, Calif.) with the following parameters: Laser 652 and 806 nm with a full bandwidth of 5 nm; LED 637 and 901 nm with full bandwidths of 17 and 69 nm respectively. The duration of treatment time for both sources was 1,800 s with a power density of 5.57 and 1.30 mW/cm$^2$ for the red and near infrared ranges respectively and with corresponding energy densities of 10.02 and 2.334 J/cm$^2$. The spot diameter from the laser source was 12.5 cm. The laser and LED power were measured with a FieldMate laser power meter (Coherent, Santa Clara, Calif.). All samples were kept under low level light or in the dark before and after irradiation.

Heat Measurements

Cell culture temperature was measured using a RAYNGER MX4 (Raytek, Santa Cruz, Calif.) infrared-detecting thermometer/laser temperature gun as previously described (see Spitler et al., Comparison of laser and diode sources for acceleration of in vitro wound healing by low-level light therapy, Journal of biomedical optics 2014, 19(3):38001). A fan was used to eliminate heat transfer from the LED circuitry. The cell culture temperature was measured before and after treatment.

Pharmacological Treatments Cells were treated with the following compounds: 50 μM sodium azide and 100 μM sodium cyanide (Sigma-Aldrich, St. Louis, Mo.) and 5 μM NO-Cbi.

Combined Pharmacological and Light Treatment

Cells were exposed to LLLT for 30 min and 1 h later received a single treatment of 5 μM NO-Cbi.

Preparation of NO-Cbi

Cobinamide was produced by base hydrolysis of hydroxocobalamin (Sigma-Aldrich, St. Louis, Mo.) as described previously (see Blackledge et al., New facile method to measure cyanide in blood, Analytical chemistry 2010, 82(10):4216-4221). The cobalt was reduced from +3 to +2 valency state using a two-molar excess of ascorbic acid in a deoxygenated solution. NO gas (99.99% pure, Matheson Gas Co.) was bubbled through the reduced cobinamide solution, and excess NO was removed by bubbling argon through the solution. Concentrated stock solutions of NO-Cbi were diluted in deoxygenated sterile water, and the diluted NO-Cbi was added to the cells using a Hamilton syringe (Hamilton, Reno, Nev.).

Scratch Wound Closure Assay

The scratch wound closure assay has been previously described (see Spitler et al., Nitrosyl-cobinamide (NO-Cbi), a new nitric oxide donor, improves wound healing through cGMP/cGMP-dependent protein kinase, Cell Signal 2013, 25(12):2374-2382). Briefly 600-700 μm wide single line scratches were mechanically generated in a cell monolayer by a 200 μl plastic tip across the length of the well. Cells from both edges of the wound migrated into the open area, which was measured at 24 h. The change in area was quantified using a custom Mat Lab script. The wound closure rate was determined by plotting changes in the wound area as a function of time.

Microscopy

Phase contrast images were captured through a 10× magnification Ph1 na (numerical aperture) 0.25 objective (Zeiss, Jena, Germany). An inverted microscope (Axiovert 135, Zeiss, Jena, Germany) with a charge-coupled device (CCD) camera (ORCA-$R^2$ Hamamatsu, Bridgewater, N.J.) was used. Images were acquired using custom Robolase II software.

Cellular ROS Detection

About $2.0 \times 10^4$ cells were seeded into each well of a black 96-well plate and allowed to attach overnight. Cells were loaded with 25 μM cell permeant reagent [2′,7′-dichloro-fluorescein diacetate, DCFDA, Abcam, Cambridge, Mass.) for 45 min. This compound detects hydrogen peroxide, superoxide and other ROS species. Cells were then washed and treated with LLLT. ROS levels were measured immediately after LLLT treatment and detected using a plate reader with a 485 nm excitation and 535 nm emission filter set.

ATP Measurement

Cells treated as described above were exposed to LLLT. Cells were extracted immediately after LLLT treatment, and the ATP concentration in the extracts was measured according to manufacturer's instructions using the ATPLite kit (PerkinElmer life sciences, Boston, Mass.).

Oxygen Consumption

A total of $1.0 \times 10^6$ intact live cells were loaded into the chamber of an Oxytherm System type Clark electrode (Hansatech Instruments, Pentney, England). Oxygen consumption rates were allowed to stabilize for 5 min prior to data acquisition by Oxygraph Plus software (Hansatech Instruments, Pentney, England). LLLT was applied to the sample while in the chamber. No respiratory substrates were added to the sample mixture as oxygen levels were measured from live cells. Oxygen consumption was measured in live cells in real time for 5 min Rate of oxygen consumption was determined using the software curve fitting function.

Cyanide Analysis

A concentration of 100 μM NaCN dissolved in 0.1 M NaOH was administered to cell cultures in a confluent 6-well dish followed by either immediate LLLT, or no treatment. After 30 min, the culture media was harvested by aspiration, and the cells were washed three times in PBS before being exacted in situ using 1 ml of RIPA Lysis and Extraction buffer (Thermo Scientific, Rockford, Ill.). A volume of 500 μl of cell extract or media was added to the outer well of a Conway microdiffusion cell and 500 μl of 10% trichloroacetic acid (TCA) was added to the opposite side of the same well to prevent premature mixing. Next a volume of 250 μl of ice-cold 30 μM cobinamide (Cbi) in 0.1 M NaOH was added to the inner well. Once the cells were capped, the TCA was mixed with the sample to convert $CN^-$ to HCN, which is volatile. The Conway cells were incubated for 25 min at room temperature to allow for the cyanide to diffuse to the center well and bind to Cbi. The solution in the center well was collected, and absorbance at 366 nm was measured using a spectrophotometer. Cyanide concentrations of the samples were determined from a standard curve.

Western Blots

Cells were lysed and harvested 10 min after LLLT treatment in Laemmli buffer heated to 100° C. (BioRad, Hercules, Calif.), and lysates were sonicated and resolved on SDS-PAGE gels. The proteins were transferred to a nitrocellulose membrane (GE Healthcare Life Sciences, Pittsburgh) and blocked for 1 h with Pierce Protein-Free Blocking buffer (Thermo Scientific, Rockford, Ill.). They were incubated overnight with antibodies for phospho-ERK1/2 (Thr202/Tyr203) at 1:10,000 in TBS/5% BSA (Cell Signaling Technology). Membranes were then incubated with an anti-rabbit-HRP antibody at 1:2000 for 1 h and developed using a luminol-based chemiluminescent substrate.

Statistical Analysis

Data are presented as mean±standard error of the mean (SEM) or mean±standard error. Student's t-tests were used for experiments that contained only two variables, and one-way analysis of variance (ANOVA) followed by Bonferroni's post-test was used for experiments containing three or more variables. A P value <0.05 was considered statistically significant.

Example 4

Figure 3:
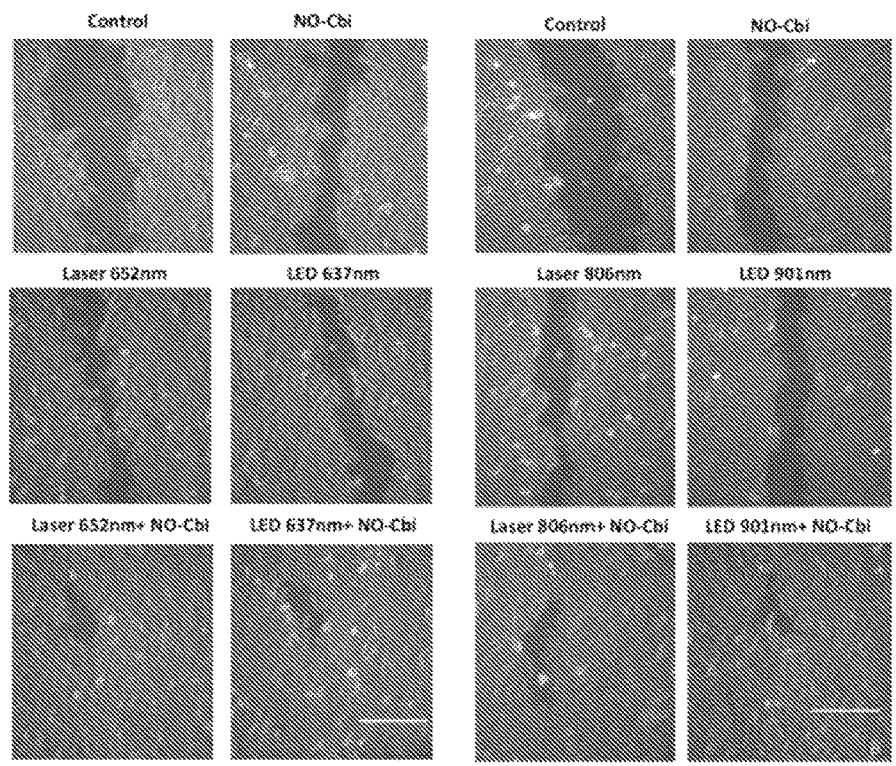
FIG. 3 depicts, in accordance with various embodiments of the invention, wound healing induced by LLLT and NO-Cbi. (A and B) U2OS cells received a mechanical scratch wound followed by treatment with LLLT, 5 μM NO-Cbi, or the combination of LLLT and NO-Cbi. Wound recovery was followed for a period of 24 h at which time the final wound area was determined and normalized to the initial wound size. The images being shown are at 24 h post treatment. The normalized average wound area was determined by dividing the final wound area by the initial wound area and averaging the replicates. The green area marks the wound. Bar, 100 μm. Data represent the mean±SEM of at least 3 separate experiments with n=12 per experiment. **$P<0.0001$, *$P<0.001$ and **$P<0.01$ compared to untreated control or indicated comparison.
Figure 3:
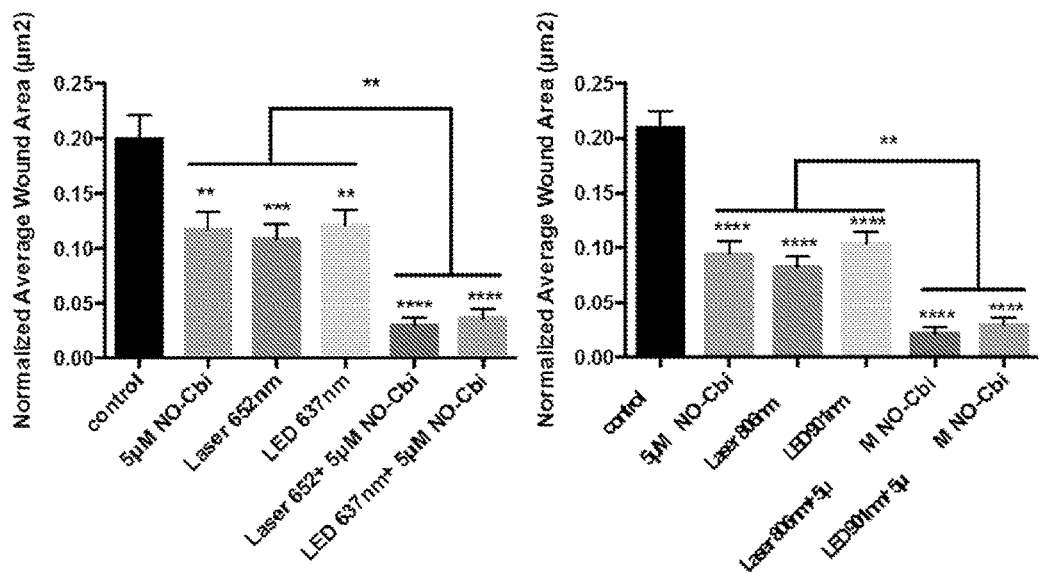

The Combination of NO-Cbi and LLLT Induces Wound Healing Much More Effectively than Either Treatment Alone NO-Cbi and LLLT enhance wound healing in cellular models (FIG. 3A, 3B). The inventors now show that combining NO-Cbi and LLLT markedly enhanced wound healing compared to either treatment alone (FIG. 3A, 3B). This effect was observed for all LLLT wavelengths tested and for light delivered by a laser or light-emitting diodes (LED).

C-ox and Electron Transport are Required for LLLT to Enhance Wound Healing

Figure 4:
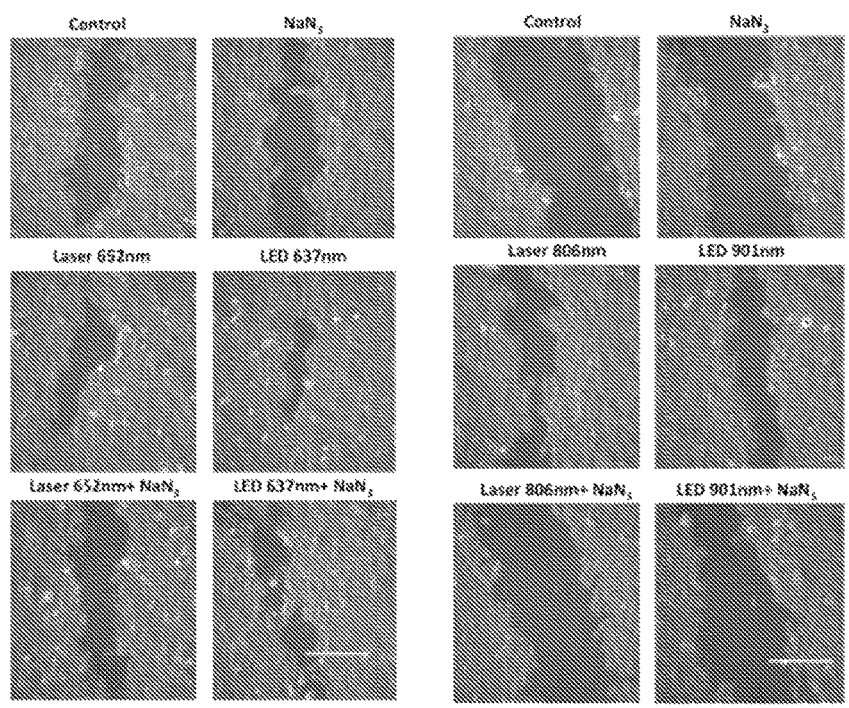
FIG. 4 depicts, in accordance with various embodiments of the invention, that sodium azide inhibits wound healing after LLLT Treatment. (A and B) A mechanical scratch wound was generated in U2OS cells, and the cells were treated with 50 μM sodium azide, a cytochrome C oxidase inhibitor. The wound closure rate was quantified after 24 h. The images being shown are at 24 h post treatment. The green area marks the wound. Bar, 100 μm. Data represent the mean±SEM of at least 3 separate experiments with n=12 per experiment. **$P<0.0001$ and *$P<0.001$ compared to untreated control.
Figure 4:
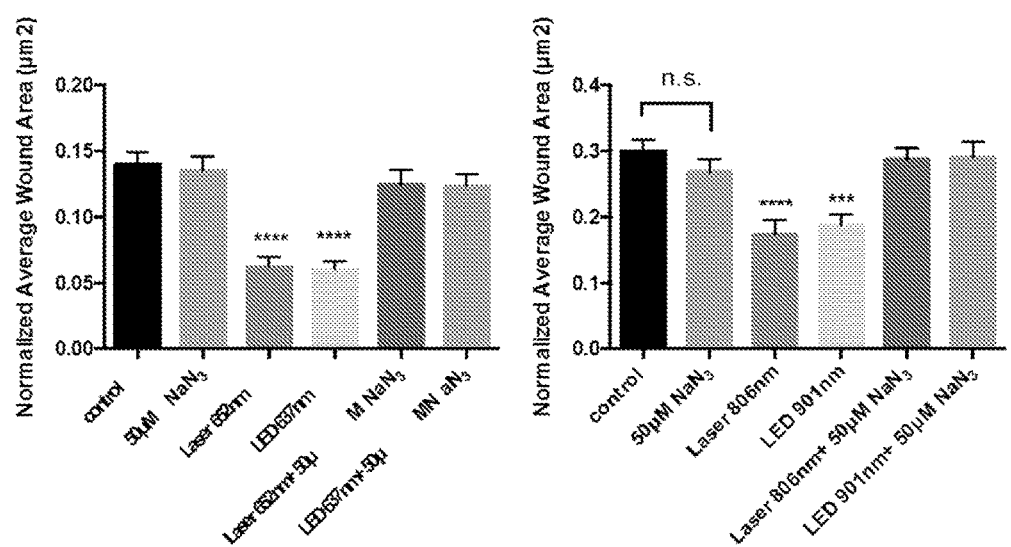
Figure 5:
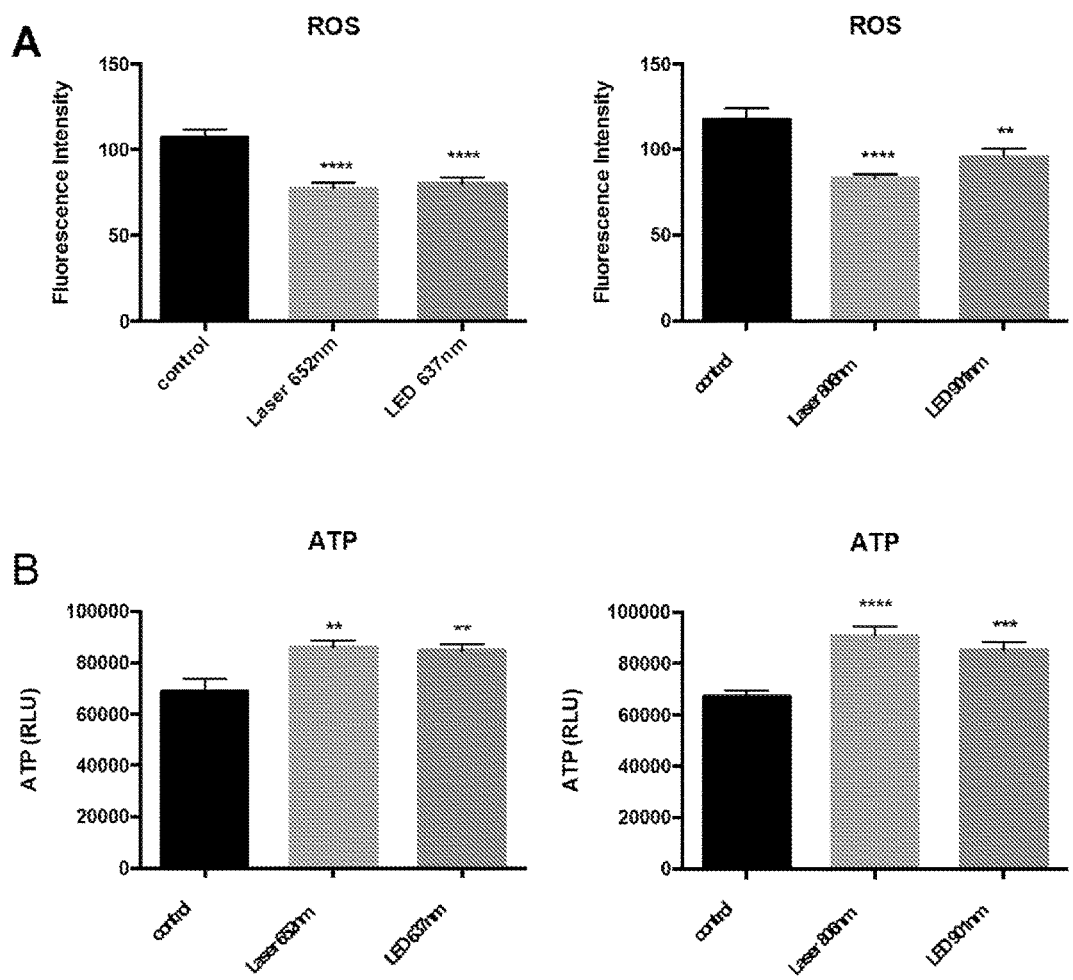
FIG. 5 depicts, in accordance with various embodiments of the invention, that LLLT reduces ROS and increases ATP concentrations. (A) U2OS cells were incubated with DCFDA dye and cellular ROS was measured as described in Methods. (B) A cell extract was prepared immediately following LLLT treatment and ATP was measured using a luciferase-based assay. Data represent the mean±SEM of at least 3 separate experiments with n=4 per experiment. **$P<0.0001$, *$P<0.001$ and **$P<0.01$ compared to untreated control.

The inventors performed several sets of experiments to determine if the effects of LLLT were mediated through the electron transport system and a C-ox-dependent mechanism. First, the inventors found that sodium azide, a C-ox inhibitor, abolished LLLT-enhanced wound healing (FIG. 4A, 4B). Second, the inventors observed increased oxygen consumption occurred almost immediately following LLLT (Table 1). Third, LLLT decreased ROS and increased ATP concentrations in U2OS cells (FIGS. 5A, 5B), indicating increased electron flow through the electron transport chain. And fourth, the inventors took advantage of the tight binding of cyanide to C-ox, and treated cells with non-toxic concentrations of cyanide, i.e., cyanide concentrations that did not reduce rates of wound healing, and then measured the intracellular cyanide concentration. The inventors found that the cyanide concentration was significantly lower in extracts of LLLT-treated cells than in control cells (Table 2). These data suggest that cyanide bound to C-ox within the cell was released when the cells were exposed to LLLT, and that the cyanide diffused into the culture media. The predicted increase in the cyanide concentration in the media was extremely small (~5 picomolar), which is below the detection limit of the assay, and, indeed, the inventors found no change in the media cyanide concentration (Table 2). The inventors provide a more in-depth explanation of this observation in the discussion section.

TABLE 1

| Treatment Condition | Oxygen Consumption Rate (nmol/1 × $10^6$ cells/min) |
| --- | --- |
| Control | 0.79 ± 0.06 |
| Laser 652 nm | 3.71 ± 0.22**** |
| Laser 806 nm | 3.42 ± 0.25**** |
| LED 637 nm | 3.46 ± 0.34**** |
| LED 901 nm | 4.30 ± 0.38**** |

Table 1: LLLT increases oxygen consumption rates. Oxygen consumption rates were measured in intact U2OS cells for 5 min, and then for an additional 5 min immediately following LLLT treatment. Data represent the mean ± SD of at least 3 separate experiments with n = 3 per experiment.
****$P < 0.0001$ compared to untreated control.

TABLE 2

| Treatment Condition | Media Cyanide Concentration (μM) | Cellular Cyanide Concentration (μM) |
| --- | --- | --- |
| Control | 5.82 ± 0.24 | 4.38 ± 0.99 |
| Laser 652 nm | 5.82 ± 0.30 | 3.04 ± 0.31** |
| Laser 806 nm | 5.84 ± 0.91 | 3.05 ± 0.72** |
| LED 637 nm | 5.80 ± 0.34 | 2.88 ± 0.53** |
| LED 901 nm | 5.79 ± 0.52 | 2.39 ± 0.15** |

Table 2: LLLT causes cyanide disassociation from C-ox. U2OS cells were treated with 100 μM sodium cyanide, and then some cells were immediately exposed to LLLT for 30 min. Media and cell extract samples were harvested and cyanide concentration was determined. Data represent the mean ± SD of at least 3 separate experiments with n = 2 per experiment.
**$P < 0.01$ compared to untreated control.

NO-Cbi-Induced ERK Activation Occurs in the Presence of LLLT

Figure 6:
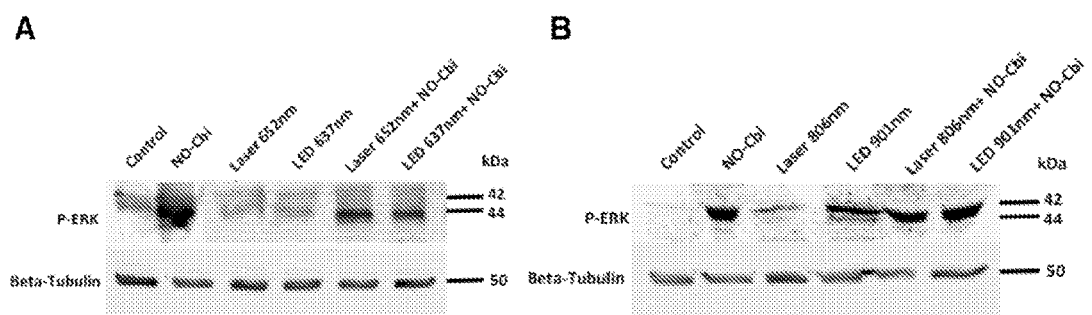
FIG. 6 depicts, in accordance with various embodiments of the invention, Western blot analysis of phosphor-Erk1/2. (A and B) U2OS cells were treated with NO-Cbi, LLLT, or a combination of LLLT and NO-Cbi. Erk 1/2 phosphorylation was determined by western blot analysis. NO-Cbi was treated alone or in combination with either 637 and 652 nm (A) or 806 or 901 nm (B). Data are representative of at least 3 separate experiments.

The inventors found that NO-Cbi increased Erk1/2 activation (FIG. 6A, 6B). LLLT in the 600 nm range had no effect on Erk1/2 activation, whereas in the 800 nm range they increased Erk1/2 activation, but less than NO-Cbi (FIGS. 6A, 6B). The combination of NO-Cbi and LLLT yielded the same degree of Erk1/2 activation as NO-Cbi alone.

The inventors identified four wavelengths of light that improved wound healing in U2OS cells, and found that the combination of light and an NO donor strikingly accelerates wound healing. LLLT decreased cellular ROS concentrations and increased cellular ATP, suggesting increased electron flow through the electron transport chain following light treatment. While a number of studies report an increase of cellular ROS resulting in activation of redox sensitive transcription factors, the inventors observed a decrease in ROS. Without wishing to be bound by any particular theory, there are at least two possible explanations for this difference in results: (1) LLLT triggered only a transient increase of ROS, which was no longer detectable after the 30 min treatment period used in our assay, or (2) LLLT triggered the up regulation of superoxide dismutase (SOD) or catalase, which would significantly reduce cellular ROS.

Data further described herein demonstrates that C-ox is the primary photo-acceptor for several reasons: (1) sodium azide, a Cox inhibitor, prevented the beneficial effect of LLLT; (2) LLLT increased oxygen consumption, and C-ox accounts for the majority of oxygen consumption within the cell; and (3) LLLT reduced intracellular cyanide, likely by releasing it from C-ox, the main cellular cyanide-binding protein. Without wishing to be bound by any particular theory, the inventors conclude that LLLT proceeds mainly through an electron transport chain-C-ox dependent mechanism. However, this does not exclude the possibility that other cellular chromophores absorb light and convert it to chemical energy. It is also possible that some of the oxygen consumption could be due to mitochondria uncoupling; however, without wishing to be bound by any particular theory, the inventors do not believe this to be the case.

Although the cyanide concentration decreased in the cell extract, no measurable change in cyanide was detected in the media. This likely can be explained as follows: a total of $1.2 \times 10^6$ cells were present in one well of a confluent cell monolayer in 1 ml of culture medium. The volume of one U2OS cell is ~4 pL, yielding a total cell volume of 4.8 μl per well. Thus, only ~5 pmol could diffuse into the cell media, which is below the detection limit of the assay.

The inventors showed that NO-Cbi improves wound healing through a cGMP/cGMP-dependent protein kinase/Erk pathway, and the inventors further demonstrate that the same degree of NO-Cbi-induced Erk activation occurs in the presence of light. Without wishing to be bound by any particular theory, the inventors conclude that NO-Cbi and LLLT improve wound healing through a cGMP/Erk and electron transport chain-C-ox pathway, respectively, with some cross talk observed when LLLT 806 nm or LED 901 nm is used. Activation of the Erk pathway has been observed in some cases in response to LLLT. However in this study Erk activation was observed only at 901 nm and possibly at 806 nm. This difference in Erk activation can be explained by the difference in cell type and optical parameters used. Low levels of nitric oxide have been associated with beneficial effects whether occurring through release from C-ox or from increased NOS activity as a result of LLLT. Without wishing to be bound by any particular theory, these findings seem to suggest that C-ox can still function normally when low concentrations of nitric oxide are present. In the current study herein, cells were first treated with LLLT, given one hour to allow for downstream effects to occur and then given a low dose of nitric oxide (5 μM) delivered by NO-Cbi. Without wishing to be bound by any particular theory, the inventors think that this delay and separation of individual treatments is what allows for the observed synergistic wound healing effect. Since nitric oxide is a known inhibitor of C-ox, adding NO-Cbi too close to the LLLT treatment will inhibit the enhanced effect observed from the combined treatment.

Without wishing to be bound by any particular theory, the inventors do not exclude the possibility that NO-Cbi and LLLT may stimulate additional pathways. This work provides clinical application for wound healing and other areas where low level light is used as a biostimulation agent.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed:

1. A method of treating a wound in a subject, comprising:
   administering nitrosyl-cobinamide (NO-Cbi) at a concentration of 3 uM to 10 uM to the subject; and
   administering a low level light therapy (LLLT) to the subject.

2. The method of claim 1, wherein the wound is chemical, thermal, mechanical, traumatic, or a combination thereof.

3. The method of claim 1, wherein the subject is a human.

4. The method of claim 1, wherein the NO-Cbi is administered about 1-3 times per day, 1-7 times per week, or 1-9 times per month.

5. The method of claim 1, wherein the NO-Cbi is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years.

6. The method of claim 1, wherein the NO-Cbi is administered in a pharmaceutical composition.

7. The method of claim 1, wherein the NO-Cbi is administered in a time release hydrogel or an aerosol spray.

8. The method of claim 1, wherein the light source of the LLLT is a laser or a LED, or a combination thereof.

9. The method of claim 1, wherein the light source of the LLLT has a bandwidth of about 1-5, 5-10, 10-20, 20-30, 30-40, 40-50, 50-60, 60-70, 70-80, 80-90, or 90-100 nm.

10. The method of claim 1, wherein the LLLT is administered at a wavelength of about 600-900 nm.

11. The method of claim 1, wherein the LLLT is administered at a wavelength of about 500-600, 600-700, 700-800, 800-900, or 900-1000 nm, or a combination thereof.

12. The method of claim 1, wherein the LLLT is administered at a wavelength of about 600-620, 620-640, 640-660, 660-680, or 680-700 nm, or a combination thereof.

13. The method of claim 1, wherein the LLLT is administered at a power density of about 0.1-1, 1-5, 5-10, 10-20, or 20-30 mW/cm$^2$.

14. The method of claim 1, wherein the LLLT is administered for about 1-10, 10-20, 20-30, 30-40, 40-50, or 50-60 minutes.

15. The method of claim 1, wherein the LLLT is administered for about 1-6, 6-12, 12-18, or 18-24 hours.

16. The method of claim 1, wherein the LLLT is administered at an energy density of about 1-5, 5-10, 10-20, 20-30, 30-40, 40-50, 50-60, 60-70, 70-80, 80-90, or 90-100 J/cm2.

17. The method of claim 1, wherein the LLLT and the NO-Cbi are administered concurrently or sequentially.

18. The method of claim 1, wherein the LLLT is administered before, during or after administering the NO-Cbi.

19. The method of claim 1, wherein the LLLT is administered about 0.1-0.5, 0.5-1, 1-6, 6-12, 12-18, or 18-24 hours before administering the NO-Cbi.

20. The method of claim 1, wherein the NO-Cbi is administered about 0.1-0.5, 0.5-1, 1-6, 6-12, 12-18, or 18-24 hours before administering the LLLT.

* * * * *